US007335688B2

(12) United States Patent
Makriyannis et al.

(10) Patent No.: US 7,335,688 B2
(45) Date of Patent: *Feb. 26, 2008

(54) BICYCLIC CANNABINOID AGONISTS FOR THE CANNABINOID RECEPTOR

(75) Inventors: Alexandros Makriyannis, Watertown, MA (US); Atmaram Khanolkar, Coventry, RI (US)

(73) Assignee: University of Connecticut, Farmington, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 11/053,132

(22) Filed: Feb. 8, 2005

(65) Prior Publication Data

US 2005/0137173 A1    Jun. 23, 2005

Related U.S. Application Data

(63) Continuation of application No. 10/110,812, filed as application No. PCT/US00/41238 on Oct. 18, 2000, now Pat. No. 6,943,266.

(60) Provisional application No. 60/160,239, filed on Oct. 18, 1999.

(51) Int. Cl.
    *A01N 35/00* (2006.01)
    *C07C 49/00* (2006.01)

(52) U.S. Cl. ...................... 514/690; 568/376

(58) Field of Classification Search ............... 568/308, 568/325, 327, 329, 326, 330, 331
    See application file for complete search history.

(56) References Cited

U.S. PATENT DOCUMENTS

| 3,041,343 A | 6/1962 | Jucker et al. |
|---|---|---|
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |
| 4,885,295 A | 12/1989 | Bell et al. |
| 5,053,548 A | 10/1991 | Tanaka et al. |
| 5,068,234 A | 11/1991 | D'Ambra et al. |
| 5,147,876 A | 9/1992 | Mizuchi et al. |
| 5,223,510 A | 6/1993 | Gubin et al. |
| 5,284,867 A | 2/1994 | Kloog |
| 5,324,737 A | 6/1994 | D'Ambra et al. |
| 5,434,295 A | 7/1995 | Mechoulam et al. |
| 5,440,052 A | 8/1995 | Makriyannis et al. |
| 5,462,960 A | 10/1995 | Barth et al. |
| 5,489,580 A | 2/1996 | Makriyannis et al. |
| 5,521,215 A | 5/1996 | Mechoulam |
| 5,532,237 A | 7/1996 | Gallant et al. |
| 5,538,993 A | 7/1996 | Mechoulam |
| 5,576,436 A | 11/1996 | McCabe et al. |
| 5,605,906 A | 2/1997 | Lau |

(Continued)

FOREIGN PATENT DOCUMENTS

EP    0276732    8/1988

(Continued)

OTHER PUBLICATIONS

Chemical Abstracts online citation [retrieved Aug. 16, 2006] Chemical Abstracts on STN, Columbus, OH, USA, Abstract No. 1978:424151.*
U.S. Appl. No. 09/600,786, filed Nov. 24, 1999, Makriyannis et al (copy not included, this is the U.S. National Phase of the Int'l Application published as WO 00/32200 enclosed herewith).
U.S. Appl. No. 10/110,865, filed Oct. 18, 2000, Makriyannis et al (copy not included, this is the U.S. National Phase of the Int'l Application published as WO 01/29007 enclosed herewith).
U.S. Appl. No. 10/110,862, filed Oct. 18, 2000 Makriyannis et al (copy not included, this is the U.S. National Phase of the Int'l Application published as WO 01/28498 enclosed herewith).

(Continued)

*Primary Examiner*—Karl Puttlitz
(74) *Attorney, Agent, or Firm*—Alix, Yale & Ristas, LLP

(57) ABSTRACT

Novel polycyclic cannabinoid analogs are presented which have preferentially high affinities for the cannabinoid CB2 receptor sites. The improved receptor affinity makes these analogs therapeutically useful as medications in individuals and animals for treatment of pain, glaucoma, epilepsy, nausea associated with chemotherapy.

20 Claims, No Drawings

U.S. PATENT DOCUMENTS

| | | | |
|---|---|---|---|
| 5,607,933 | A | 3/1997 | D'Ambra et al. |
| 5,618,955 | A | 4/1997 | Mechoulam et al. |
| 5,624,941 | A | 4/1997 | Barth et al. |
| 5,631,297 | A | 5/1997 | Pate et al. |
| 5,635,530 | A | 6/1997 | Mechoulam |
| 5,688,825 | A | 11/1997 | Makriyannis et al. |
| 5,744,459 | A | 4/1998 | Makriyannis et al. |
| 5,747,524 | A | 5/1998 | Cullinan et al. |
| 5,804,601 | A | 9/1998 | Kato et al. |
| 5,817,651 | A | 10/1998 | D'Ambra et al. |
| 5,872,148 | A | 2/1999 | Makriyannis et al. |
| 5,874,459 | A | 2/1999 | Makriyannis et al. |
| 5,925,628 | A | 7/1999 | Lee et al. |
| 5,925,768 | A | 7/1999 | Barth et al. |
| 5,932,610 | A | 8/1999 | Shohami et al. |
| 5,939,429 | A | 8/1999 | Kunos et al. |
| 5,948,777 | A | 9/1999 | Bender et al. |
| 6,013,648 | A | 1/2000 | Rinaldi et al. |
| 6,028,084 | A | 2/2000 | Barth et al. |
| 6,096,740 | A | 8/2000 | Mechoulam |
| 6,127,399 | A | 10/2000 | Yuan |
| 6,166,066 | A | 12/2000 | Makriyannis et al. |
| 6,284,788 | B1 | 9/2001 | Mittendorf et al. |
| 6,391,909 | B1 | 5/2002 | Makriyannis et al. |
| 6,579,900 | B2 | 6/2003 | Makriyannis et al. |
| 6,610,737 | B1 | 8/2003 | Garzon et al. |
| 6,653,304 | B2 | 11/2003 | Leftheris et al. |
| 6,864,291 | B1 | 3/2005 | Fride et al. |
| 6,900,236 | B1 | 5/2005 | Makriyannis et al. |
| 6,903,137 | B2 | 6/2005 | Fride et al. |
| 6,939,977 | B2 | 9/2005 | Makriyannis et al. |
| 6,943,266 | B1 | 9/2005 | Makriyannis et al. |
| 6,995,187 | B1 | 2/2006 | Makriyannis et al. |
| 2003/0149082 | A1 | 8/2003 | Makriyannis et al. |
| 2004/0077649 | A1 | 4/2004 | Makriyannis et al. |
| 2004/0077851 | A1 | 4/2004 | Makriyannis et al. |
| 2004/0087590 | A1 | 5/2004 | Makriyannis et al. |
| 2004/0192667 | A1 | 9/2004 | Makriyannis et al. |
| 2004/0236101 | A1 | 11/2004 | Makriyannis et al. |
| 2004/0236116 | A1 | 11/2004 | Makriyannis et al. |
| 2005/0020679 | A1 | 1/2005 | Makriyannis et al. |
| 2005/0074408 | A1 | 4/2005 | Makriyannis et al. |
| 2005/0119234 | A1 | 6/2005 | Makriyannis et al. |
| 2005/0137173 | A1 | 6/2005 | Makriyannis et al. |
| 2005/0239874 | A1 | 10/2005 | Makriyannis et al. |
| 2006/0030563 | A1 | 2/2006 | Makriyannis et al. |
| 2006/0100208 | A1 | 5/2006 | Makriyannis et al. |

FOREIGN PATENT DOCUMENTS

| | | |
|---|---|---|
| EP | 0444451 | 9/1991 |
| EP | 0471609 | 6/1993 |
| EP | 0576357 | 12/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| NL | 6509930 | 2/1966 |
| WO | WO 94/12466 | 6/1994 |
| WO | WO 97/00860 | 1/1997 |
| WO | WO 97/21682 | 6/1997 |
| WO | WO 97/45407 | 12/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |
| WO | WO 01/28497 | 4/2001 |
| WO | WO 01/28498 | 4/2001 |
| WO | WO 01/28557 | 4/2001 |
| WO | WO 01/29007 | 4/2001 |
| WO | WO 01/32169 | 5/2001 |
| WO | WO 01/58869 | 8/2001 |
| WO | WO 02/12167 | 2/2002 |
| WO | WO 02/058636 | 8/2002 |
| WO | WO 02/060447 | 8/2002 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |
| WO | WO 04/017920 | 3/2004 |
| WO | PCT/US2005/036524 | 10/2005 |
| WO | PCT/US2006/000720 | 1/2006 |

OTHER PUBLICATIONS

U.S. Appl. No. 11/344,762, filed Dec. 29, 2005, Makriyannis et al.

U.S. Appl. No. 11/323,560, filed Dec. 26, 2005, Makriyannis et al.

Abadji V., Lin S., Taha G., Griffin G., Stevenson L.A., Pertwee R.G., Makriyannis A.; "(R)-Methanadamide: a chiral novel anandamide possessing higher potency and metabolic stability"; J. Med. Chem.; 37(12); 1889-1893; Jun. 10, 1994.

Alo, B.I.; Kandil, A.; Patil, P. A.; Sharp, M. J.; Siddiqui, M. A.; and Snieckus, V. Sequential Directed Ortho Metalation-Boronic Acid Cross-Coupling Reactions. A general Regiospecific Route to Oxygenated Dibenzo[b,d]pyran-6-ones Related to Ellagic Acid, J. Org. Chem. 1991, 56, 3763-3768.

Archer et al; "cannabinoids, synthesis approaches to 9-ketocannabinoids."; J. Org. Chem.; vol. 42; No. 13; 2277-2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104-106. (abstract only).

Barnett-Norris et al; "Exploration of biologically relevant conformations of anandamide, . . . "; J. Med. Chem.; vol. 41; 4861-4872; 1998.

Beak, P.; and Brown, R.A., The Tertiary Amide as an Effective Director of Ortho Lithiation, J. Org. Chem. 1982, 47, 34-36.

Belgaonkar et al; "Isocoumarins. XIV. synthesius of 3-benzylisocoumarins and 3-benzyl-1(2H)-isoquinolones."; Indian J. Chem; vol. 13; No. 4; 336-338; 1975 (abstract only).

Beltramo M., Stella N., Calignano A., Lin S. Y., Makriyannis A., Piomelli D; "Functional Role Of High-Affinity Anandamide Transport, as Revealed By Selective Inhibition"; Science; vol. 277; 1094-1097; 1997.

Beltramo M., Stella N., Calignano A., Lin S. Y., Makriyannis A., Piomelli D; "Identification and Functional Role of High Affinity Anandamide Transport"; Soc. Neurosci. Abstr. 23:137 (1997). (1 page).

Beltramo M., Piomelli D; "Anandamide Transport Inhibition by the Vanilloide Agonist Olvanil"; Europeean J. of Pharmacology; (1999); 364(1); 75-78 (abstract only).

Berdyshev EV, Cannabinoid receptors and the regulation of immune response. Chem Phys Lipids. Nov. 2000; 108(1-2):169-90.

Berglund et al; "Structural requirements for arachidonylethanolamide interaction with CB1 and CB2 cannabinoid receptors: . . . "; Prostanglandins, leukotrienes ands essential fatty acids; 59(2); 111-118; (1998).

Bodnar, V.N., Lozinskii, M.O., Pel'kis, P.S.; "Synthesis fo 2,5-disubstituted 1,3,4-oxadiazoles and 1,4-dihydro-1,2,4,5-tetrazines"; Ukrainskii Khimicheskii Zhurnal (Russian Edition); 48(12); 1308-1311; 1982 (abstract only).

Bracey, M et al, Structural Adaptations in a Membrane Enzyme That Terminates Endocannabinoid Signaling. Science 2002; 298(5599): 1793-1796.

Brenneisen R, Pgli A, Elshohly MA, Henn V. Spiess Y: The effect of orally and rectally administered Δ9—tetrahydrocannabinol on spasticity, a pilot study with 2 patients. Int. J. Clin Pharmacol Ther. (1996) 34:446-452. (abstract only).

Brotchie JM: Adjuncts to dopamine replacement a pragmatic approach to reducing the problem of dyskinesia in Parkinson's disease. Mov. Disord. (1998) 13:871-876. (abstract only).
Brown et al; "Synthesis and hydroboration of (-)-2-phenylapopinen, Comparison of mono(2-phenylapoisopinocampheyl)borane with its 2-methyl and 2-ethyl analogues for the chiral hydroboration of representative alkenes"; J. Org. Chem.; 55(4); 1217-1223; (1990).
Buckley NE, McCoy KI, Mpzey E et al, "Immunomodulation by cannabinoids is absent in mice deficient for the cannabinoid CB2 receptor"; Eur. J Pharmacol (2000) 396:141-149.
Burstein et al; "detection of cannabinoid receptors . . . "; Biochem. Biophys. Res, Commun.; vol. 176(1); 492-497; 1991 (abstract only).
Busch-Peterson et al; "Unsaturated side chain beta-11-hydroxyhexahydrocannabinol analogs"; J. Med. Chem.; 39; 3790-3796; (1996).
Calignano A, La Rana G. Diuffrida A, Piomelli D; "Control of pain initiation by endogenous cannabinoids"; Nature (1998) 394:277-291. (abstract only).
Calignano A., La Rana G., Beltramo, M., Makriyannis A., Piomelli D; "Potentiation of Anandamide Hypotension by the Transport Zinhibitor, AM404"; Eur. J. Pharmacol.; 1997; 337 R1-R2.
Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7-R8.
Campbell FA et al; "Are cannabinoids an effective and safe treatment option in the management of pain? A qualitative systematic review"; BMJ. Jul. 7, 2001;323(7303):13-6.
Charalambous A. et al; "5'-azido Δ8-THC: A Novel Photoaffinity Label for the Cannabinoid Receptor"; J. Med. Chem., 35, 3076-3079 (1992).
Charalambous A. et al; "Pharmacological evaluation of halogenated . . . "; Pharmacol. Biochem. Behav.; vol. 40; No. 3; 509-512; 1991.
Cheng et al; "Relationship Between the Inhibition Constant (Ki) and the concentration of Inhibitor which causes 50% Inhibition (IC50) of an Enzymatic Reaction"; Biochem. Pharmacol., 22, 3099-3102, (1973) (abstract only).
Cherest M., Luscindi X.; "The action of acetyl chloride and of acetic anhydride on the lithium nitronate salt of 2-phenylnitroethane . . . "; Tetrahedron; 42(14); 3825-3840; 1986; in French with English abstract.
Cherest M., Lusinchi X.; "A novel electrophilic N-amidation via electron deficient complexes: action of ferric chloride on N-acetyloxyamides"; Tetrahedron Letters; 30(6); 715-718; 1989.
Colombo G, Agabio R, Diaz G. et al; "Appetite suppression and weight loss after the cannabinoid antagonist SR141716"; Life Sci. (1998) 63-PL13-PL117. (abtsract only).
Compton D.R. et al; "Pharmacological Profile Of A Series Of Bicyclic Cannabinoid Analogs: Classification as Cannabimimetic Agents"; J. Pharmacol. Exp. Ther.; 260; 201-209; 1992. (abstract only).
Compton et al; "Synthesis and pharmacological evaluation of ether and related analogues of delta8-. delta9- and delta9,11-tetrahydrocannabinol"; J. Med. Chem; vol. 34; No. 11; 3310-3316; 1991.
Consroe P, Musty R, Rein J, Tillery W, Pertwee R; "The perceived effects of smoked cannabis on patents with multiple sclerosis"; Eur. Neurol. (1997) 38-44-48 (abstract only).
Coxon et al; "Derivatives of nopinone"; Aust. J. Chem.; 23; 1069-1071; (1970) (abstract only).
Crawley et al; "Anandamide, an endogenous ligand of the cannabinoid receptor, induces hypomotility and hypothermia in vivo in rodents"; Pharmacology Biochemistry and Behavior; vol. 46; 967-972; 1993.
Croce, P. D. et al; "Reactions of Hydrazonoyl Halides with Imidazoles and Benzimidesazoles"; J.C.S. Perkin I; vol. 2; 330-332; (1979).
Croce, P. D. et al; "Reaction of Thiete 1,1-Dioxide with alpha-Chlorobenzalphenylhydrazine and Methyl Phenylhydrazonochloroacetate"; Journal of Heterocyclic Chemistry; vol. 15, No. 3; 515-517; (1978).

D'Ambra et al; "C-attached aminoalkylindoles: potent cannabinoid mimetics"; Bioorg. & Med. Chem. Lett., 1996, 6(1), 17-22.
D'Amour F.E. et al; "A Method For Determining Loss Of Pain Sensation"; J. Pharmacol. Exp. Ther.; 72; 74-79; 1941.
Demuynck L. et al; "Rearrangement of Indolo[2,3-a]quinolizidines to derivatives with E-azaaspidospermane skeleton"; Tetrahedron Letters; 30(6) 710-722; 1989; in French with English abstract.
DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375-8380.
Desarnaud F., Cadas H., Piomelli D.; "Anandamide amidohyrolase activity in rat brain microsomes"; J. Biol. Chem.; 270; 6030-6035; (1995).
Deutsch D.G. et al; "Fatty acid sulfonyl fluorides inhibit anandamide metabolism and bind to cannabinoid receptor"; Biochem. Biophys. Res. Commun. 231(1); 217-221; 1997; CODEN: BBRCA9; ISSN:0006-291X; XP002040933.
Deutsch D.G., Chin S.A.; "Enzymatic synthesis and degradation of anandamide, a cannabinoid receptor agonist"; Biochemical Pharmacology; 46(5); 791-796; 1993.
Devane, W.A. et al; "Determination and Characterization of a Cannabinoid Receptor in a Rat Brain"; Mol. Pharmacol., 34, 605-613 (1988). (abstract only).
Di Marzo, V., Melck, D., Bisogno, T., DePetrocellis, L.; "Endocannabinoids: endogenous cannabinoid receptor ligands with neuromodulatory action"; Trends Neurosci. (1998) 21:521-528.
Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449-454. (abstract only).
Dodd, P.R. et al, A Rapid Method for Preparing Synaptosomes: Comparison with Alternative Procedures, Brain Res., 226, 107-118 (1981). (abstract only).
Dominiami et al; "Synthesis of 5-(tert-Alkyl)resorcinols"; J. Org. Chem. 42(2); 344-346; (1977).
Drake et al, "classical/nonclassical hydrid cannabinoids"; J. Med. Chem.; vol. 41(19); 3596-3608 (1998).
Edery et al; "Activity of novel aminocannabinoids in baboons"; J. Med. Chem.; 27; 1370-1373 (1984).
Eissenstat et al; "Aminoalkylindoles: structure-activity relationships of novel cannabinoid mimetics"; J. Med. Chem. 1995, vol. 38, No. 16, pp. 3094-3105; XP 000651090.
Fahrenholtz, K. E., Lurie, M. and Kierstead, AR. W.; "The Total Synthesis of dl-Δ9-Tetrahydrocannabinol and Four of Its Isomers"; J. Amer. Chem. Soc. 1967, 89(23), 5934-5941.
Fahrenholtz; "The synthesis of 2 metabolites of (-)-delta eight-tetrahydrocannabinol"; J. Org. Chem.; vol. 37(13); 1972; XP002111824.
Fisera, L., Kovac, J., Lesco, J., Smahovsky, V.; "Furan derivatives. Part CLVI. 1,3-dipolar cycloadditions of heterocycles. V. Reaction of C-acetyl-N-phenylnitrilimine with furan derivatives"; Chemicke Zvesti; 35(1); 93-104 1981 (abstract only).
Fride, E. & Mechoulam, R.; "Pharmacological activity of the cannabinoid receptor agonist, anandamide, a brain constituent"; European Journal of Pharmacology, vol. 231; 313-314; 1993.
Galiegue S et al. ; "Expression of central and peripheral cannabinoid receptors in human immune tissues and leukocyte subpopulations"; Eur J Biochem.; Aug. 15, 1995;232(1):54-61. (abstract only).
Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189-194.
Gold et al; "A comparison of the discriminative stimulus properties of delta9-tetrahydrocannabinol and CP 55,940 in rats and rhesus monkeys"; J. Pharmacol. Exp. Ther.; vol. 262(2); 479-486; 1992.
Green K.; "Marijuana smoking vs. cannabinoids for glaucoma therapy."; Arch. Ophthamol. (1998) Nov. 116(11); 1433-1437. (abstract only).
Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117-125.

Hampson, A.J., Grimaldi M. Axpirod J. Wink D; "Cannabidiol and (-) Δ9 tetrahydrocannabinol are neuroprotective antioxidants"; Proc. Natl Acad Sci. USA (Jul. 1998) 95; 8268-8273.

Hanus et al; "Two new unsaturated fatty acids ethanolamides in brain that bind to the cannabinoid receptor"; Journal of medicinal Chemistry; 36(20); 3032-3034; 1993.

Hargreaves, K. et al; "A new sensitive method for measuring thermal nociception in cutaneous hyperalgesia"; Pain; 32; 77-88; (1988) (abstract only).

Hemming M, Yellowlees PM; "Effective treatment of Tourette's syndrome with marijuana"; J. Psychopharmacol, (1993) 7:389-391.

Herzberg U, Eliav E, Bennett GJ, Kopin IJ; "The analgesic effects of R(+)WIN 55,212-2 mesylate, a high affinity cannabinoid agonist in a rat model of neuropathic pain"; Neurosci. Letts. (1997) 221; 157-160.

Hillard C. J., Edgemond, W. S., Jarrahian W., Campbell, W. B.; "Accumulation of N-Arachidonoylethanolamine (Anandamine) into Cerebellar Granule Cells Occurs via Facilitated Diffusion"; Journal of Neurochemistry; 69; 631-638 (1997).

Horrevoets A.J.G et al; "Inactivation of Escherichia coli outer membrane phospholipase A by the affinity label hexadecanesulfonyl fluoride"; Eur. J. Biochem.; 198; 247-253; 1991.

Horrevoets A.J.G et al; "Inactivation of reconstituted Escherichia coli outer membrane phospholipase A by membrane-perturbing peptides results in an increased reactivity towards the affinity label hexadecanesulfonyl fluoride"; Eur. J. Biochem.; 198; 255-261; 1991.

Howlett et al; "Azido and isothicyanato substituted aryl pyrazoles bind covalently to the CB1 cannabinoid receptor and impair signal transduction"; Journal of Neurochemistry; vol. 74(5) (2000) 2174-2181; XP001097394.

Howlett et al; "Stereochemical effects of 11-OH-delta 8 tetrahydrocannabinol-dimethylheptyl to inhibit adenylate cyclase and bind to the cannabinoid receptor"; Neuropharmacology; vol. 29(2); 161-165; 1990.

Huffman et al; "3-(1',1'-dimethylbutyl)—deoxy-delta 8THC and related compounds: synthesis of selective ligands for the CB2 receptor"; Bioorganic and Medicinal Chemistry; vol. 7; 2905-2914; (1999).

Huffman et al; "Stereoselective synthesis of the epimeric delta 7-tetrahydocannabinols"; tetrahedron; vol. 51(4); 1017-1032; (1995).

Huffman et al; "Synthesis of 5',11 dihydroxy delta 8 tetrahydrocannabinol"; Tetrahedron, vol. 53(39), pp. 13295-13306 (1997).

Huffman et al; "Synthesis of a tetracyclic, conformationally constrained analogue of delta8-THC"; Bioorganic & Medicinal Chemistry; vol. 6(12); 2281-2288; 1998; XP002123230.

Huffman et al; "Synthesis of both enantiomers of Nabilone from a common intermediate. Enantiodivergent synthesis of cannabinoids"; J. Org. Chem.; 1991, 56, 2081-2086.

Huffman et al; "A Pyridone Analogue of Traditional Cannabinoids. A New Class of Selective Ligands For The CB2 Receptor."; Biorg. Med. Chem.; vol. 9(11), Nov. 2001; 2863-2870. (abstract only).

Jbilo, O., Derocq, J., Segui, M., Le Fur, G., Casellas, P.; "Stimulation of peripheral cannabinoid receptor CB2 induces MCP-1 and IL-8 gene expression in human promyelocytic cell line HL60"; FEBS LETTERS; (1999); vol. 448; No. 21848; 273-277.

Joy JE, Wagtson SJ, Benson JA; "Marijuana and Medicine Assessing the Science Base"; National Academy Press, Washington, DC, USA (1999). (abstract only).

Kaminski NE; "Regulation of the cAMP cascade, gene expression and immune function by cannabinoid receptors"; J Neuroimmunol. Mar. 15, 1998;83(1-2):124-32.

Kawase M. et al; "Electrophilic aromatic substitution with N-methoxy-N-acylnitrenium ions generated from N-chloro-N-methoxyamides: synthesis of nitrogen heterocyclic compounds bearing a N-methoxyamide group"; J. Org. Chem.; 54; 3394-3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515-4519; (1996).

Khanolkar et al; "Molecular probes for the cannabinoid receptors"; Chemistry and Physics of Lipids; 108; 37-52; (2000).

Klein T.W. et al, "The cannabinoid system and cytokine network"; Proc Soc Exp Biol Med. Oct. 2000; 225(1):1-8; (abstract only).

Klein TW et al, "Cannabinoid receptors and immunity"; Immunol Today; Aug. 1998; 19(8):373-81.

Koutek B. et al; "Inhibitors of arachidonyl ethanolamide hydrolysis"; J. Biol. Chem.; 269(37); 22937-40; 1994; CODEN: JBCHA3; ISSN: 0021-9258; XP002040931.

Kumar RN, et al; "Pharmacological actions and therapeutic uses of cannabis and cannabinoids"; Anesthesia, 2001, 56: 1059-1068 (abstract only).

Lan, R et al; "Structure activity relationships of pyrazole derivatives as cannabinoid receptor antagonists"; J. Med. Chem.; vol. 42(4); 769-776; (1999).

Lang, W., Qin, C., Hill, W.A., Lin, S., Khanolkar, A.D., Makriyannis, A.; High-Performance Liquid Chromatographic Determination of Anandamide Amidase Activity in Rat Brain Microsomes; Anal. Biochem; (1996), 238, 40-45 (abstract only).

Lang, W. et al; "Substrate Specificity and Stereoselectivity of Rat Brain Microsomal Anandamide Amidohydrolase"; J. Med. Chem.; vol. 42(5); 896-902; (1999).

Lavalle et al; "Efficient conversion of (1R, 5R)-(+)-alpha-pinene to (1S, 5R)-(-)-nopinene"; J. Org. Chem.; vol. 51(8); 1362-1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure-Activity Studies Related to 1,2-Dimethylheptyl Derivatives"; J. Med. Chem.; vol. 16(11); 1200-1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635-2637; 1990 (abstract only).

Ludt, R.E. et al; "A comparison of the synthetic utility of n-butyl-lithium and lithium diisopropylamide in the metalations of N,N-dialkyltouamides"; J. Org. Chem.; 38(9); 1668-1674 (1973).

Maccarron M., Endocannabinoids and their actions. Vitamins and Hormones 2002; 65:225-255.

Mackie K., Devane W.A., Hille B.; "Anandamide, an endogenous cannabinoid, inhibits calcium currents as a partial agonist in N18 neuroblastoma cells"; Mol. Pharmacol; 44; 498-0503 (1993).

Markwell, M.A.K., S.M. Haas, L.L. Bieber, and N.E. Tolbert.; "A modification of the Lowry procedure to simplify protein determination in the membrane and lipoprotein samples." 1978; Anal. Biochem. 87:206-210.

Martin et al; "Behavioral, biochemical, and molecular modeling evaluations of cannabinoids analogs"; Pharmacol. Biochem. Behav.; vol. 40(3); 471-478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1-amino-and 1 mercapto-7,8,9,10-tetrahydro-6h-dibenzo[b,d]pyrans"; J. of Med. Chem.; vol. 20(1); 17-24; 1977; XP00211825.

Maurer M, Henn V, Dittrich A, Hofmann A.; "Delta-9-tetrahydrocannabinol shows antispastic and analgesic effects in a single case double-blind trial."; Eur. Arch. Psychiat. Clin. Neurosci. (1990), 240:1-4. (abstract only).

Mavromoustakos, T. et al; "Studies on the thermotropic effects of cannabinoids on phosphatidylcholine bilayers using differential scanning calorimetry and small angle X-ray diffraction"; Biochimica et Biophysica Acta; vol. 1281(2); 235-244; 1996; XP002111823.

Mechoulam et al; "Stereochemical Requirements for cannabinoid activity"; J. Med. Chem.; 23(10); 1068-1072; (1980).

Mechoulam et al; "Structural Requirements for Binding of Anandamide Type Compounds to the Brain Cannabinoid Receptor"; J. Med. Chem.; 40; 659-667 (1997).

Mechoulam et al; "Synthesis of the individual, pharmacologically distinct, enantiomers of a tetrahydrocannabinol derivative"; Tetrahedron Asymmetry; 1: 315-318; (1990) (abstract only).

Mechoulam, "Cannabinoids as therapeutic agents"; CRC press, 1986.

Mechoulam et al; "Towards Cannabinoids drugs—Revisited"; Progress in Medicinal Chemistry; 35; 199-243; Jul. 3, 1998.

Melck, D, Bisogno, T., DePetrocellis, L., Chuang, H., Julius, D., Bifulco, M., DiMarzo, V.; "Unsaturated Long-Chain N-Acyl-vanillyl-amides"; Biochemical and Biophysical Res. Commun.; (1999); 262(1); 275-284 (abstract only).

Meltzer et al; "An improved synthesis of cannabinol and cannabiorcol"; Synthesis; 1981:985 (1981).

Melvin et al; "Structure-Activity Relationships Defining the ACD-Tricyclic Cannabinoids Cannabinoid Receptor Binding and Analgesic Activity"; Drug Design and Discovery; 13(2); 155-166 (1995). (abstract only).

Melvin et al; "Structure-activity relationships for cannabinoids receptor-binding and analgesic activity: studies of bicyclic cannabinoids analogs"; Mol. Pharmacol.; 44(5); 1008-1015 (1993) (abstract only).

Merck Index; 11th edition; "Tetrahydrocannabinols" compound No. 9142; 1989.

Meschler, J. P., Kraichely, D. M., Wilken, G. H., Howlett, A. C.; "Inverse Agonist Properties of N-(Piperidin-1-yl)-5-(4-chlorophenyl)-1-(2,4-dichlorophenyl)-4-methyl-1H-pyrazole-3-carboxamide HCL (SR141716A) and 1-(2-Chlorophenyl)-4-cyano-5-(4-methoxyphenyl)-1H-pyrazole-3-carboxylic Acid Phenylamide (CP-272871) for the CB1 Cannabinoids Receptor"; Biochemical Pharmacology; (2000); vol. 60; No. 9; 1315-1322.

Molteni, G. et al; "Nitrilimine Cycloadditions in Aqueous Media"; J.C.S. Perkins I; vol. 22; 3742-3745; (2000).

Morgan Dr: Therapeutic Uses of Cannabis. Harwood Academic Publishers, Amsterdam. (1997).

Morris, S.; Mechoulam, R.; and Irene, Y., *Halogenation of phenols and Phenyl ethers with Potassium Halides in the Presence of 18-Crown-6 on Oxidation with m-Chloroperbenzoic Acid*, J. Chem. Soc., Perkin Trans. 1 1987, 1423-1427.

Muller-Vahl KB, Kolbe H, Schneider U, Emrich, HM Cannabis in movement disorders. Porsch. Kompicmentarmed (1999) 6 (suppl. 3) 23-27. (abstract only).

Muller-Vahl KB, Schneider U, Kolbe H, Emrich, HM.; "Treatment of Tourette's syndrome with delta-9-tetrahydrocannabinol." Am. J. Psychiat.; (1999); 156(3); 495.

Nahas G, Marijuana and Medicine; 1999, *Human Press Inc.*, Totowa, NJ.

Neunhoeffer O., Gottschlich R.; "Acylating activity of O-acylated hydroxylamine derivatives"; Justus Leibigs Ann. Chem.; 736; 100-109; 1970; in German with English abstract.

Ng et al; "Unique Analogues of Anandamide: Arachidonyl Ethers and Carbamates and Norarachidonyl Carbamates and Ureas"; J. Med. Chem.; 1999; 42(11); 1975-1981.

Novak, J et al; Cannabis, part 27, synthesis of 8-, 10- and 11-oxygenated cannabinoids; J. Chem. Soc. Perkin Trans.; 2867-2871; (1983) (abstract only).

Nye et al; "High affinity cannabinoid binding sites in brain membranes labelled with [H]-5'-trimethylammonium delta8-tetrahydrocannabinol"; J. Pharmacol. Exp. Ther.; vol. 234(3); 784-791; 1985.

Pacheco M, et al; "Aminoalkylindoles: Actions On Specific G-Protein-Linked Recpetors"; J. Pharmacol. Exp. Ther.; vol. 257, No. 1, pp. 170-183 (1991).

Palmer et al; "Natural and Synthetic Endocannabinoids and Their Structure-Activity Relationships"; Current Pharmaceutical Design; 6; 1381-1397; (2000).

Papahatjis et al; "A new ring-forming methodology for the synthesis of conformationally constrained bioactive molecules"; Chemistry Letters, 192; (2001).

Papahatjis et al; "Pharmacophoric requirements for cannabinoid side chains: multiple bond and C1'-substituted delta8-tetrahydrocannabinols"; J. Med. Chem.; 41(7); 1195-1200; (1998).

Pertwee et al; "AM630, a competitive cannabinoids receptor agonist"; Life Sci. 1995, 56(23/24), 1949-1955; XP 000653566.

Pertwee et al; "Pharmacological characterization of three novel cannabinoid receptor agonists in the mouse isolated vas deferens"; Eur. J. Pharmacol. 1995, 284, 241-247; XP-001041044.

Pertwee et al; "Inhibitory effects of certain enantiomeric cannabinoids in the mouse vas deferens and the myenteric plexus preparation of guinea-pig small intestine"; Br. J. Pharmacol.; 105(4); 980-984 (1992). (abstract only).

Pertwee; Pharmacology of cannabinoids CB1 and CB2 receptors; Pharmacol. Ther., vol. 74(2); pp. 129-180; (1997); XP002226467.

Petrov, M.L., Terent'eva, N.A., Potekhin, K.A., Struchkov, Yu. T.; ".alpha.,.beta.-unsaturated thiolates and their analogs in cycloaddition reactions. XVIII. Reaction of (2-phenylethynyl)tellurolates with C-ethoxycarbonyl-N-Phenylnitrilimine"; Zhurnal Organicheskoi Khimii; 29(7); 1372-1378; (1993) (abstract only).

Pinnegan-Ling D, Musty R.; *Marinol and phantom limb pain: a case study. Proc Inv. Cannabinoid Rea. Sec.* (1994):53.

Pinto et al; Cannabinoid Receptor Binding and Agonist Activity of Amides and Esters of Arachidonic Acid; Mol. Pharmacol.; 1994; 46(3); 516-522.

Piomelli D., Beltramo M., Glasmapp S., Lin S.Y., Goutopoulos A., Xiw X-Q., Makriyannis A.; "Structural determinants for recognition and translocation by the anandamide transporter"; Proc. Natl. Acad. Sci. USA; 96; 5802-5807; (1999).

Pitt et al; "The synthesis of Deuterium, carbon-14 and carrier free tritium labelled cannabinoids"; Journal of Labelled Compounds; vol. 11(4); 551-575; 1975; XP002123229.

Porreca F., Mosberg H.I., Hurst R., Hruby V.J., Burks T.F.; "Roles of mu, delta and kappa opiod receptors in spinal and supraspinal mediation of gastrointestinal transit effects and hot-plate analgesia in the mouse"; J. Pharmacol. Exp. Ther.; 230(2); 341-348; (1994). (abstract only).

Quere, L., Boigegrain, R., Jeanjean, F., Gully, D., Evrard, G., Durant, F.; "Structural requirements of non-peptide neurotensin receptor antagonists"; J. Chem Soc., Perkin Trans. 2, (1996); 2639-2646.

Razdan et al; "Drugs derived from cannabinoids. 6. .Synthesis of cyclic analogues of dimethylheptylpyran"; J. Med. Chem.; vol. 19(5); 719-721; 1976 (abstract only).

Razdan et al; "Pharmacological and Behavioral Evaluation of Alkylated Anandamide Analogs"; Life Sci.; 1995; 56(23-24); 2041-2048.

Reggio et al; "Characterization of a region of steric interference at the cannabinoid receptor using the active analog approach"; J. Med. Chem. United States; vol. 36(12); 1761-1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoids Receptors and Inhibiton of Adenylcyclase"; J. Med. Chem. 1997, 40(20); 3228-3233.

Rice AS. Cannabinoids and pain. Curr Opin Investig Drugs. Mar. 2001;2(3):399-414. (abstract only).

Richardson JD, Aanonsen I, Hargreaves KM; "Antihyperalgesic effects of a spinal cannabinoids"; Eur. J. Pharmacol. (1998) 346:145-153.

Richardson JD, Kilo S. Hargreaves KM; "Cannabinoids reduce dryperalgesia and inflammation via interaction with peripheral CB1 receptors"; Pain (1998) 75:111-119.

Rinaldi-Carmona et al; "Biochemical and pharmacological characterization of SR141716A, the first potent and selective brain cannabinoid receptor antagonist"; Life Sci.; vol. 56(23/24); 1941-1947 (1995).

Rinaldi-Carmona et al; "SR141716A, a potent and selective antagonist of the brain cannabinoid receptor"; FEBS Lett.; 350; 240-244; (1994).

Rompp Chemie Lexikon; Falbe and Regitz; "band 1-A-C1, 8"; Aufl, Thieme Verlag; Stuttgart, S 569-570; 1989.

Santus, Maria; "Studies on thioamides and their derivatives. IX. Synthesis of the derivatives of 1,2,4,5-tetrazine"; Acta Polonae Pharmaceutica; 50(2-3); 183-188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278-87.

Schuel, H., Burkman, L.J., Picone, R.P., Bo, T., Makriyannis, A., *Cannabinoids receptors in human sperm. Mol. Biol. Cell.*, (1997) (8), 325a.

Serdarevich B., Caroll K.K., "Synthesis and characterization of 1- and 2-monoglycerides of anteiso fatty acids"; J. Lipid Res.; 7; 277-284; (1966).

Shawali, A.S., Albar, H.A.; "Kinetics and mechanism of dehydrochlorination of N-aryl-C-ethoxycarbonyl formohydrazidoyl chlorides"; Canadian Journal of Chemistry; 64(5); 871-875; 1986 (abstract only).

Shen M. Thayer SA: Cannabinoid receptor agonists protect cultured rat hippocampal neurons from excitotoxicity. Mol. Pharmacol (1996) 54:459-462.

Sheskin, T. et al; Structural Requirements for Binding of Anandamide Type Compounds to the Brain Cannabinoid Receptor; J. Med. Chem.; 1997; 40; 659-667.

Shim et al; "Three-dimensional quantitative structure-activity relationship study of the cannabimimetic (aminoalkyl)indoles using comparative molecular field analysis"; J. Med. Chem.; 1998, 41(23); 4521-4532; XP-002212407.

Shim et al; "Unified pharmacophoric model for cannabinoids and aminoalkylindoles derived from molecular superimposition of CB1 cannabinoid receptor agonists CP55244 and WIN55212-2"; ACS Symposium series, 1999 719 (rational drug design), 165-184; XP-001095771.

Shiue, J-S et al; "Phenyl-Carbonyl Coupling Reactions Promoted by Samarium Diiodide and Hexamethylphosphoramide"; J. Org. Chem.; vol. 62, No. 14; 4643-4649; (1997).

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989-999; XP-001097918.

Simiand J, Keane M, Keane PE, Soubrie P: SR 141716, A CB1 cannabinoid receptor antagonist, selectivity reduces sweet food intake in marmoset. Behav. Pharmacol (1998) 9:179-181. (abstract only).

Smith P.B. et al; "The pharmacological activity of anandamide, a putative endogenous cannabinoid, in mice"; Journal of Pharmacology and Experimental Therapeutics; vol. 270(1):219-227; 1994.

Terranova J-P, Storme J-J Lafon N et al; "Improvement of memory in rodents by the selective CB1 cannabinoid receptor antagonist, SR 141716"; Psychopharmacol (1996) 126:165-172 (abstract only).

Tetko, I. V. et al; "Volume Learning Algoritm Artificial Neural Networks For 3D QSAR Studies"; J. Med. Chem.; vol. 44, No. 15 (2001) pp. 2411-2420.

Tewari, R. S. et al; "1,3-Dipolar Cycloadditions and Nucleophilic Substitution Reactions of C-Acetyl and C-Ethoxycarbonyl Derivative of Hydrazidoyl Bromides"; Tetrahedron; vol. 39, No. 1; 129-136; (1983).

Tius et al; "Conformationally restricted hybrids of CP-55,940 and HHC: Steroeselective synthesis and activity"; Tetrahedron; 50 (9); 2671-2680; (1994) (abstract only).

Twitchell, W. et al; "Cannabinoids inhibit N- and P/Q type calcium channels in cultured rat hippocampal neurons"; Journal of Neurophysiology; 78(1); 43-50; 1997 (abstract only).

Ueda, N., Endocannabinoid hydrolases. Prostaglandins & Other Lipid Mediators 2002;68-69:521-534 (abstract only).

Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352-355; (1993) (abstract only).

Wagner JA, Varga K, Jarai Z, Kunos G; "Mesenteric Vasodilation Mediated by Endothelia Anandamide Receptors"; Hypertension (1999) 33:429-434.

Watanabe, T.; Miyaura, N.; and Suzuki, A.; "Synthesis of Sterically Hindered Biaryls via the Palladium Catalyzed Cross-Coupling Reaction of Arylboronic Acids or their Esters with Haloarenes"; Synlett 1992, 207-210.

Wiley et al; "Structure activity relationships of indole and pyrrole derived cannabinoids"; J. Pharmacol. Exp. Ther. 1998, 285(3), 995-1004; XP-001097982.

Wilson et al; "9-nor-delta8-tetrahydrocannabinol, a cannabinoid of metabolic intersts"; J. Med. Chem.; 17(4); 475-476; (1974).

Wilson et al; "Analgesic properties of the tetrahydrocannabinols, their metabolites and analogs"; J. Med. Chem.; 18(7); 700-703; (1975).

Wilson et al; "9-nor-9-hydrohexahydrocannabinols. Synthesis, some behavioral and analgesic properties, and comparison with the tetrahydrocannabinols"; J. Med. Chem.; 19(9); 1165-1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967-1974.

Yan, Guo et al; "Synthesis and pharmacological properties of 11-hydroxy-3-(1'-1'-dimethylheptyl)hexahydrocannabinol: a high affinity cannabinoid agonist"; J. Med. Chem.; vol. 37(16); 2619-2622; (1994).

Yan Guo et al; "(-)-11-hydroxy-7'-isothiocyanato-1'-1'dimethylheptyl-delta8-THC: a novel probe for the cannabinoid receptor in the brain"; J. Med. Chem.; 37(23); 3867-3870; (1994).

Supplementary European Search Report for Application No. EP 00 98 4533 dated Feb. 22, 2005.

* cited by examiner

BICYCLIC CANNABINOID AGONISTS FOR THE CANNABINOID RECEPTOR

This application is a continuation of U.S. patent application Ser. No. 10/110,812, filed Oct. 21, 2002, now U.S. Pat. No. 6,943,266 which was the National Stage of International Application No. PCT/US00/41238, filed Oct. 18, 2000, which claims the benefit of U.S. Provisional Patent Application No. 60/160,239, filed Oct. 18, 1999, the contents of each of which are incorporated herein by reference in their entirety.

FIELD OF THE INVENTION

The present invention relates generally to cannabinoid compounds and is more particularly concerned with new and improved cannabinoid compounds exhibiting high binding affinity and selectivity for the CB1 and CB2 cannabinoid receptors, pharmaceutical preparations employing these analogs and methods of administering therapeutically effective amounts of the preparations to provide a physiological effect.

BACKGROUND OF THE INVENTION

Classical cannabinoids such as the marijuana derived cannabinoid $\Delta^9$-tetrahydrocannabinol, ($\Delta^9$-THC) produce their pharmacological effects through interaction with specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects. See, for example, Pertwee, R. G., *Pharmacology of cannabinoid CB1 and CB2 receptors*, Pharmacol. Ther., (1997) 74:129-180 and Di Marzo, V., Melck, D., Bisogno, T., DePetrocellis, L., *Endocannabinoids: endogenous cannabinoid receptor ligands with neuromodulatory action*, Trends Neurosci. (1998) 21:521-528.

There is considerable interest in developing cannabinoid analogs possessing high affinity for one of the CB1 or CB2 receptors. Such analogs may offer a rational therapeutic approach to a variety of disease states.

SUMMARY OF THE INVENTION

The inventive compounds have been found to act as agonists for the CB1 and CB2 receptors. The invention includes compounds selective for either the CB1 or CB2 receptors. Certain of the novel bicyclic cannabinoids possess surprisingly improved cannabinoid receptor affinity and/or specificity over known cannabinoids. Thus, one aspect of the invention is the novel cannabinoids represented by structural formula 1 and physiologically acceptable salts thereof.

structural formula 1

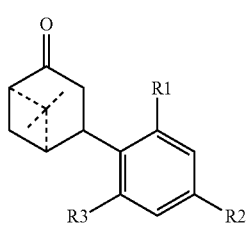

wherein $R_1$ is selected from the group consisting of OH; H; OCH$_3$; N$_3$; NH$_2$; O(CH$_2$)$_n$N(CH$_3$)$_2$ and

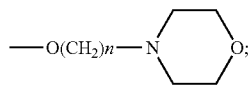

where n is an integer from 1-3;
$R_2$ is selected from the group consisting of (CH$_2$)$_n$CH$_3$, where n is an integer from 4-6; C(CH$_3$)$_2$(CH$_2$)$_n$CH$_3$, where n is an integer from 3-5;

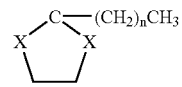

where X is selected from the group consisting of C, O, S and NH and n is an integer from 3-5; (CH$_2$)$_n$C≡C where n is an integer from 3-5; C≡C(CH$_2$)$_n$CH$_3$ where n is an integer from 2-4 and

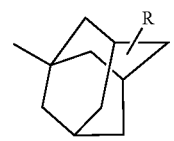

where R is (CH$_2$)$_n$CH$_3$, where n is a maximum of 7; and
$R_3$ is selected from the group consisting of H; OH; OCH$_3$; N$_3$ and O(CH$_2$)$_n$OH; where n is an integer from 1-5.

The novel cannabinoids are also more polar (less lipophilic) then known cannabinoids, which can improve their therapeutic usefulness in certain applications. Therefore, the novel compounds described herein, and physiologically acceptable salts thereof, represent potentially useful materials for providing a physiological effect to treat pain; peripheral pain; glaucoma; epilepsy; nausea such as associated with cancer chemotherapy; AIDS Wasting Syndrome; cancer; neurodegenerative diseases including Multiple Sclerosis, Parkinson's Disease, Huntington's Chorea and Alzheimer's Disease; to enhance appetite; to reduce fertility; to prevent or reduce diseases associated with motor function such as Tourette's syndrome; to prevent or reduce inflammation; to provide neuroprotection and to suppress memory and produce peripheral vasodilation. Thus, another aspect of the invention is the administration of a therapeutically effective amount of an inventive compound, or a physiologically acceptable salt thereof, to an individual or animal to provide a physiological effect.

DESCRIPTION OF SOME PREFERRED EMBODIMENTS

As used herein a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Physiological effects that result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

The novel cannabinoids can generally be described with reference to structural formula 1 and include physiologically acceptable salts thereof.

structural formula 1

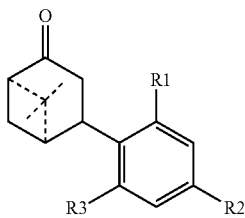

wherein $R_1$ is selected from the group consisting of OH; H; $OCH_3$; $N_3$; $NH_2$; $O(CH_2)_nN(CH_3)_2$ and

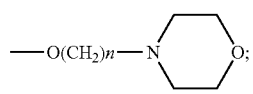

where n is an integer from 1-3;
$R_2$ is selected from the group consisting of $(CH_2)_nCH_3$, where n is an integer from 4-6; $C(CH_3)_2(CH_2)_nCH_3$, where n is an integer from 3-5;

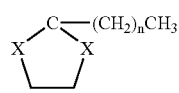

where X is selected from the group consisting of C, O, S and NH and n is an integer from 3-5; $(CH_2)_nC\equiv C$ where n is an integer from 3-5; $C\equiv C(CH_2)_nCH_3$ where n is an integer from 2-4 and

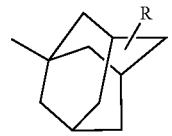

where R is $(CH_2)_nCH_3$, where n is a maximum of 7; and
$R_3$ is selected from the group consisting of H; OH; $OCH_3$; $N_3$ and $O(CH_2)_nOH$; where n is an integer from 1-5.

The following examples are given for purposes of illustration only in order that the present invention may be more fully understood. These examples are not intended to limit in any way the practice of the invention. Material AM1703 was prepared. Material AM1703 can be represented by structural formula 1 when $R_1$ and $R_3$ are each OH and $R_2$ is 1,1-dimethylheptyl. Material AM1703 is shown in structural formula 2.

structural formula 2

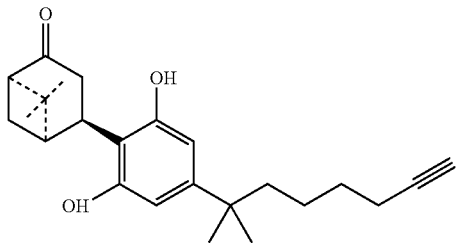

Material AM1703 was prepared as follows.

[7-(3,5-Dimethoxyphenyl-1,3-dithian-7-yl)-1-heptynyl]trimethysilane.

A solution of 5 g (19.5 mmol) of 2-(3,5-dimethoxyphenyl)-1,3-dithiane in 38 mL of dry tetrahydrofuran was cooled to −30° C. under argon and 14.5 mL of a 1.6 M solution (23.5 mmol) of n-butyllithium in hexanes was added dropwise. The yellow-brown reaction mixture was stirred at the same temperature for 2 hours (h) and 5.43 g (23.4 mmol, neat) of (6-bromo-1-hexynyl)trimethysilane was added in a dropwise manner when the color changed from yellow-brown to light yellow. The reaction mixture was allowed to warm to room temperature overnight and poured into water and extracted with diethyl ether. The combined organic extracts were dried and ether removed to afford the crude product which was purified on silica gel (15% diethyl ether-petroleum ether) to afford 6.81 g (86%) of the title compound as an oil. Anal. calcd. for $C_{21}H_{32}O_2S_2Si$ C, 61.72; H, 7.89.

[7-(3,5-Dimethoxyphenyl)-7-oxo-1-heptynyl]trimethylsilane.

A solution of 6.40 g (15.8 mmol) of [7-(3,5-dimethoxyphenyl-1,3-dithian-7-yl)-1-heptynyl]trimethysilane in 160 mL of 10% aqueous methanol was cooled in an ice-bath and 10.2 g (23.7 mmol, 1.5 equiv.) of bis(trifluoroacetoxy)iodobenzene was added portionwise with stirring. The reaction mixture was stirred for an additional 10 min and poured into 100 mL of sodium bicarbonate solution. The mixture was extracted with diethyl ether, ether extracts were combined, dried and ether removed to afford an oil which was chromatographed on silica gel to afford 4.5 g (90%) of the title compound. Anal. calcd. for $C_{18}H_{26}O_3Si$ C, 67.88; H, 8.23.

[7-(3,5-Dimethoxyphenyl)-7-methyl-1-octynyl]trimethysilane.

[7-(3,5-Dimetho-xyphenyl)-7-oxo-1-heptynyl]trimethysilane (1.50 g, 4.75 mmol) was dissolved in 10 mL of anhydrous ether, the solution was cooled in an ice-bath under argon and a 3.16 mL of a 3 M solution of methylmagnesium bromide (9.48 mmol) in ether was added dropwise. The light grey solution was allowed to warm to room temperature and stirred for an additional hour. The reaction mixture was poured into saturated ammonium chloride solution, the organic phase was separated and the aqueous phase was extracted with fresh diethyl ether. The combined ether extracts were dried and ether removed to afford 1.50 g (95%) of pure [7-(3,5-dimethoxyphenyl)-7-hydroxy-1-octynyl]trimethysilane as a viscous oil after passing through a short silica gel column.

The above tertiary carbinol (1.50 g, 4.52 mmol) was dissolved in 9 mL of anhydrous carbon tetrachloride and dry hydrogen chloride gas was bubbled through for 1 h. The solution was transferred to a separatory funnel with the aid of more carbon tetrachloride, washed with water and 10% sodium bicarbonate solution. The organic phase was dried and rotary evaporated to afford an oil which was passed through a short silica column to give 1.43 g (90%) of the pure [7-chloro-7-(3,5-dimethoxyphenyl)-1-octynyl]trimethysilane.

A solution of the above chloride (1.43 g, 4.08 mmol) in dry toluene was cooled to −30° C. under argon and 4.1 mL of a 2 M solution of trimethylaluminum in toluene was added in a slow dropwise manner. The resulting clear reaction mixture was stirred at room temperature for about 16 hours and then 5% aqueous hydrochloric acid was added in a very cautious manner. The organic layer was separated, washer with water, dried and toluene removed. The residual oil was chromatographed on silica gel to afford a colorless oil. Anal. calcd. for $C_{20}H_{32}O_2Si$ C, 72.23; H, 9.70.

7-(3,5-Dimethoxyphenyl)-7-methyl-1-octyne (8-065).

[7-(3,5-Dimethoxyphenyl)-7-methyl-1-octynyl]trimethysilane (900 mg, 2.73 mmol) was dissolved in 3.5 mL of anhydrous methanol. Anhydrous potassium carbonate (75 mg, 0.55 mmol, 20 mol %) was added and the heterogeneous mixture was stirred at room temperature, under argon, for 24 h. The reaction mixture was diluted with water and extracted with diethyl ether. The ether extract was dried, concentrated by rotary evaporation and the residue was purified by chromatography on silica gel (5% ethyl ether-petroleum ether) to give 540 mg (76%) of the desilylated product. Anal. calcd. for $C_{17}H_{24}O_2$ C, 78.42; H, 9.29.

3-(1,1-Dimethylhept-6-ynyl)resorcinol (8-065).

A solution of 7-(3,5-dimethoxyphenyl)-7-methyl-1-octyne (445 mg, 1.71 mmol) in 17 mL of anhydrous dichloromethane was cooled to −40° C. under argon and 4.3 mL of a 1 M solution of boron tribromide (4.30 mmol) was added via syringe. The reaction mixture was allowed to warm to 0° C. with stirring over a period of 1-1.5 h and then quenched with saturated sodium bicarbonate. The organic layer was separated, dried and solvent removed. The residue was chromatographed on silica gel (30-40% ethyl ether-petroleum ether) to give 224 mg (56%) of the title resorcinol. Anal. calcd. for $C_{15}H_{20}O_2$ C, 77.55; H, 8.68.

Coupling of 3-(1,1-dimethylhept-6-ynyl)resorcinol with nopinone diacetate.

A mixture of 224 mg (0.97 mmol) of 3-(1,1-dimethylhept-6-ynyl)resorcinol, 270 mg (0.97 mmol) nopinone diacetate and 185 mg (0.97 mmol) of p-toluenesulfonic acid monohydrate in 10 mL of chloroform was allowed to stand at room temperature for 4 h as described by Archer et al. After confirming the completion of the reaction by TLC, the reaction mixture was transferred to a separatory funnel and washed successively with 10% sodium bicarbonate, water, and dried. Solvent was removed and the residue was purified by flash chromatography on silica gel (30-40% ethyl ether-petroleum ether) to give 140 mg (40%) of the title bicyclic ketone (AM1703).

As used herein, "binding affinity" ($K_i$) is represented by the $IC_{50}$ value which is the concentration of an analog required to occupy the 50% of the total number (Bmax) of the receptors. The lower the $IC_{50}$ value the higher the binding affinity. As used herein an analog is said to have "binding selectivity" if it has higher binding affinity for one receptor compared to the other receptor; e.g. a cannabinoid analog which has an $IC_{50}$ of 0.1 nanomoles (nM) for CB1 and 10 nM for CB2, is 100 times more selective for the CB1 receptor. The AM1703 material was tested for CB2 receptor binding affinity and for CB1 receptor affinity (to determine selectivity for the CB2 receptor).

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107-118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605-613 (1988) and A. Charalambous et al, *5'-azido $\Delta^8$ -THC: A Novel Photoaffinity Label for the Cannabinoid Receptor*, J. Med. Chem., 35, 3076-3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at a pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials at 30° C. for 1 hour. The samples were filtered using Packard Filtermate 196 and Whatman GF/C filterplates and washed with wash buffer (TME containing 0.5% BSA). Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the using the assumptions of Cheng et al, *Relationship Between*

*the Inhibition Constant ($K_i$) and the concentration of Inhibitor which causes 50% Inhibition ($IC_{50}$) of an Enzymatic Reaction*, Biochem. Pharmacol., 22, 3099-3102, (1973), which is incorporated by reference herein.

For the CB2 receptor binding studies, membranes were prepared from frozen mouse spleen essentially according to the procedure of P. R. Dodd et al, *A Rapid Method for Preparing Synaptosomes: Comparison with Alternative Procedures*, Brain Res., 226, 107-118 (1981) which is incorporated by reference herein. Silanized centrifuge tubes were used throughout to minimize receptor loss due to adsorption. The CB2 binding assay was conducted in the same manner as for the CB1 binding assay.

Binding affinities ($K_i$) for both the CB1 and CB2 receptors are typically expressed in nanomoles (nM), although novel compound AM1703 surprisingly exhibited a CB2 affinity of 0.59 picomoles (pM) and about a 500-fold CB2 selectivity over CB1. Other cannabinoid analogs have been reported that show some selectivity for the CB2 receptor. However the inventive analog described herein has surprisingly high affinity and selectivity for the CB2 receptor.

The physiological and therapeutic advantages of the inventive materials can be seen with additional reference to the following references, the disclosures of which are hereby incorporated by reference. Arnone M., Maruani J., Chaperon P, et al, *Selective inhibition of sucrose and ethanol intake by SR141716, an antagonist of central cannabinoid (CB1) receptors*, Psychopharmacal, (1997) 132, 104-106. Colombo G, Agabio R, Diaz G. et al: *Appetite suppression and weight loss after the cannabinoid antagonist SR141716*. Life Sci. (1998) 63-PL13-PL117. Simiand J, Keane M, Keane P E, Soubrie P: *SR 141716, A CB1 cannabinoid receptor antagonist, selectively reduces sweet food intake in marmoset*. Behav. Pharmacol (1998) 9:179-181. Brotchie J M: *Adjuncts to dopamine replacement a pragmatic approach to reducing the problem of dyskinesia in Parkinson's disease*. Mov. Disord. (1998) 13:871-876. Terranova J-P, Storme J-J Lafon N et al: *Improvement of memory in rodents by the selective CB1 cannabinoid receptor antagonist*, SR 141716. Psycho-pharmacol (1996) 126:165-172. Hampson A L Grimaldi M. Axpirod J. Wink D: *Cannabidiol and (-) $\Delta^9$ tetrahydrocannabinol are neuroprotective antioxidants*. Proc. Natl Acad Sci. USA (1998) 9S:8268-8273. Buckley N E, McCoy K I, Mpzey E et al *Immunomodulation by cannabinoids is absent in mice deficient for the cannabinoid $CB_2$ receptor*. Eur. J Pharmacol (2000) 396:141-149. Morgan Dr: *Therapeutic Uses of Cannabis*. Harwood Academic Publishers, Amsterdam. (1997). Joy J E, Wagtson S J, Benson J A: *Marijuana and Medicine Assessing the Science Base*. National Academy Press, Wash., D.C., USA (1999). Shen M. Thayer S A: *Cannabinoid receptor agonists protect cultured rat hippocampal neurons from excitotoxicity*. Mol. Pharmacol (1996) 54:459-462. DePetrocellis L, Melck D, Palmisano A. et al: *The endogenous cannabinoid anandamide inhibits human breaast cancer cell proliferation*. Proc Natl. Acad. Sci USA (1998) 95:8375-8380. Green K. *Marijuana smoking vs. cannabinoids for glaucoma therapy*; Arch. Ophibalmol. (1998) feb 433-1437. Hemming M, Yellowlees P M, *Effective treatment of Tourette's syndrome with marijuana*. J. Psychopharmacol, (1993) 7:389-391. Muller-Vahl KB, Schneider U, Kolbe H, Emrich, H M. *Treatment of Tourette's syndrome with delta-9-tetrahydrocannabinol*. Am. J. Psychiat. (1999) 156-195. Muller-Vahl K B, Kolbe H, Schneider U, Emrich, H M *Cannabis in movement disorders*. Porsch. Kompicmentarmed (1999) 6 (suppl. 3) 23-27. Consroe P, Musty R, Rein J, Tillery W, Pertwee R. *The perceived effects of smoked cannabis on patents with multiple sclerosis*, Eur. Neurol. (1997) 38-44-48. Pinnegan-Ling D, Musty R. *Marinol and phantom limb pain: a case study*. Proc Inv. Cannabinoid Rea. Sec. (1994): 53. Brenneisen R, Pgli A, Elsohly M A, Henn V. Spiess Y: *The effect of orally and rectally administered $\Delta^9$-tetrahydrocannabinol on spasticity, a pilot study with 2 patients*. Int. J. Clin Pharmacol Ther. (1996) 34:446-452. Martyn C N. Illis L S, Thom J. *Nabilone in the treatment of multiple sclerosis*. Lancet (1995) 345:579. Maurer M, Henn V, Dittrich A, Hofmann A. *Delta-9-tetrahydrocannabinol shows antispastic and analgesic effects in a single case double-blind trial*. Eur. Arch. Psychiat. Clin. Neurosci. (1990), Z40:1-4. Herzberg U, Eliav E, Bennett G J, Kopin I J: *The analgesic effects of R(+) WIN 55,212-2 mesylate, a high affinity cannabinoid agonist in a rare model of neuropathic pain*. Neurosci. Letts. (1997) 221:157-160. Richardson J D, Kilo S. Hargreaves K M, *Cannabinoids reduce dryperalgesia and inflammation via interaction with peripheral CB1 receptors*. Pain (1998) 75:111-119. Ricardson J D, Aanonsen I, Hargreaves K M: *Antihyperalgesic effects of a spinal cannabinoids*. Eur. J. Pharmacol. (1998) 346:145-153. Calignano A, La Rana G. Diuffrida A, Piomelli D: *Control of pain initiation by endogenous cannabinoids*. Nature (1998) 394: 277-291. Wagner J A, Varga K, Jarai Z, Kunos G: *Mesenteric vasodilation mediated by endothelia anandamide receptors*. Hypertension (1999) 33:429-434. Schuel, H., Burkman, L. J., Picone, R. P., Bo, T., Makriyannis, A., *Cannabinoid receptors in human sperm*. Mol. Biol. Cell., (1997) (8), 325a.

The inventive analogs described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer; neurodegenerative diseases including Multiple Sclerosis, Parkinson's Disease, Huntington's Chorea and Alzheimer's Disease; to enhance appetite; to reduce fertility; to prevent or reduce diseases associated with motor function such as Tourette's syndrome; to prevent or reduce inflammation; to provide neuroprotection and to suppress memory and produce peripheral vasodilation. Thus, another aspect of the invention is the administration of a therapeutically effective amount of an inventive compound, or a physiologically acceptable salt thereof, to an individual or animal to provide a physiological effect.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A method of providing a physiological effect in an individual or animal conferred by activating a cannabinoid receptor in that individual or animal comprising administering to the individual or animal a pharmaceutical composition including a therapeutically effective amount of a compound having the formula:

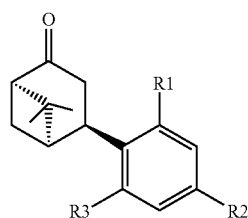

and physiologically acceptable salts of the compound, wherein $R_1$ is selected from OH; H; $OCH_3$; $N_3$; $NH_2$; $O(CH_2)_nN(CH_3)_2$ and

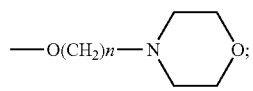

where n is an integer from 1-3;

$R_2$ is selected from $C(CH_3)_2(CH_2)_4C\equiv CH$; $(CH_2)_nCH_3$, where n is an integer from 4-6; $C(CH_3)_2(CH_2)_nCH_3$, where n is an integer from 3-5;

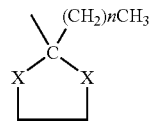

where each X is independently selected from $CH_2$, O, S and NH and n is an integer from 3-5;

$(CH_2)_nC\equiv CH$ where n is an integer from 3-5; $C\equiv C(CH_2)_nCH_3$ where n is an integer from 2-4 and

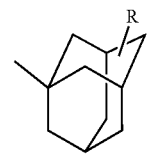

where R is $(CH_2)_nCH_3$, and n is a maximum of 7; and $R_3$ is selected from H; OH; $OCH_3$; $N_3$ and $O(CH_2)_nOH$; where n is an integer from 1-5.

2. The method of claim 1 wherein $R_1$ and $R_3$ are each OH and $R_2$ is 1,1-dimethylheptyl.

3. The method of claim 1 wherein:

$R_1$ is selected from OH; $NH_2$; $O(CH_2)_nN(CH_3)_2$ and

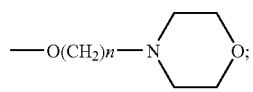

where n is an integer from 1-3;

$R_2$ is selected from $C(CH_3)_2(CH_2)_nCH_3$, where n is an integer from 3-5;

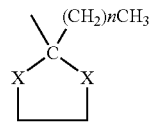

where each X is independently selected from $CH_2$, O, S and NH and n is an integer from 3-5; and

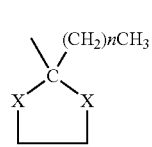

where R is $(CH_2)_nCH_3$, and n is a maximum of 7; and $R_3$ is selected from H; OH; $OCH_3$; $N_3$ and $O(CH_2)_nOH$; where n is an integer from 1-5.

4. The method of claim 1 wherein $R_2$ is selected from $(CH_2)_nC\equiv CH$ where n is an integer from 3-5, $C\equiv C(CH_2)_nCH_3$ where n is an integer from 2-4,

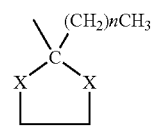

where each X is independently selected from $CH_2$, O, S and NH and n is an integer from 3-5, and

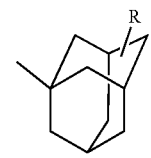

where R is $(CH_2)_nCH_3$ and n is a maximum of 7.

5. A method of activating a cannabinoid receptor in an individual or animal comprising administering to the individual or animal a pharmaceutical composition including a therapeutically effective amount of at least one compound having the formula:

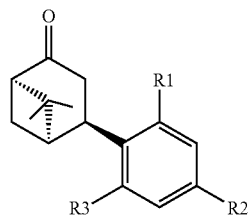

or a physiologically acceptable salt of the compound, wherein $R_1$ is selected from OH; H; $OCH_3$; $N_3$; $NH_2$; $O(CH_2)_nN(CH_3)_2$ and

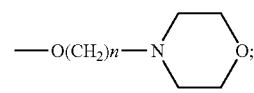

where n is an integer from 1-3;

$R_2$ is selected from $C(CH_3)_2(CH_2)_4 C\equiv CH$; $(CH_2)_nCH_3$, where n is an integer from 4-6; $C(CH_3)_2(CH_2)_nCH_3$, where n is an integer from 3-5;

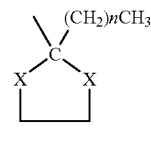

where each X is independently selected from $CH_2$, O, S and NH and n is an integer from 3-5;

$(CH_2)_nC\equiv CH$ where n is an integer from 3-5; $C\equiv C(CH_2)_nCH_3$ where n is an integer from 2-4 and

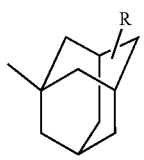

where R is $(CH_2)_nCH_3$, and n is a maximum of 7; and
$R_3$ is selected from H; OH; $OCH_3$; $N_3$ and $O(CH_2)_nOH$; where n is an integer from 1-5.

6. The method of claim 5 wherein:
$R_1$ is selected from OH; $NH_2$; $O(CH_2)_nN(CH_3)_2$ and

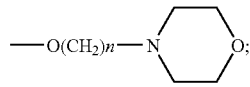

where n is an integer from 1-3;
$R_2$ is selected from $C(CH_3)_2(CH_2)_nCH_3$, where n is an integer from 3-5;

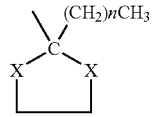

where each X is independently selected from $CH_2$, O, S and NH and n is an integer from 3-5; and

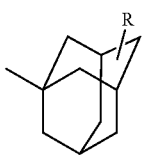

where R is $(CH_2)_nCH_3$, and n is a maximum of 7; and
$R_3$ is selected from H; OH; $OCH_3$; $N_3$ and $O(CH_2)_nOH$; where n is an integer from 1-5.

7. The method of claim 5 wherein $R_2$ is selected from $(CH_2)_nC\equiv CH$ where n is an integer from 3-5, $C\equiv C(CH_2)_nCH_3$ where n is an integer from 2-4,

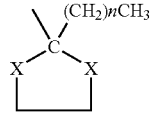

where each X is independently selected from $CH_2$, O, S and NH and n is an integer from 3-5, and

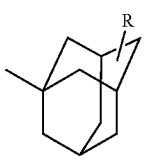

where R is $(CH_2)_nCH_3$ and n is a maximum of 7.

8. A method of treating a condition responsive to activation of a cannabinoid receptor by a cannabinoid agonist in an individual or animal having that condition comprising administering to the individual or animal having the condition a pharmaceutical composition including a therapeutically effective amount of at least one compound having the formula

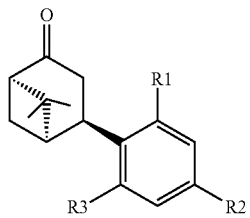

or a physiologically acceptable salt of the compound, wherein:
$R_1$ is selected from OH; H; $OCH_3$; $N_3$; $NH_2$; $O(CH_2)_nN(CH_3)_2$ and

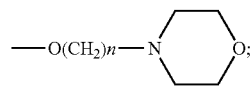

where n is an integer from 1-3;
$R_3$ is selected from H; OH; $OCH_3$; $N_3$ and $O(CH_2)_nOH$; where n is an integer from 1-5; and
$R_2$ is selected from $C(CH_3)_2(CH_2)_4C\equiv CH$; $(CH_2)_nC\equiv CH$ where n is an integer from 3-5, $C\equiv C(CH_2)_nCH_3$ where n is an integer from 2-4,

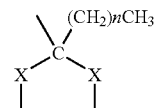

where each X is independently selected from $CH_2$, O, S and NH and n is an integer from 3-5,

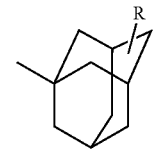

where R is $(CH_2)_nCH_3$ and n is a maximum of 7, $C(CH_3)_2(CH_2)_nCH_3$, where n is an integer from 3-5, and $(CH_2)_nCH_3$, where n is an integer from 4-6.

9. The method of claim 8 wherein $R_2$ is selected from $(CH_2)_nC\equiv CH$ where n is an integer from 3-5, $C\equiv C(CH_2)_nCH_3$ where n is an integer from 2-4,

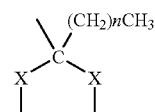

where each X is independently selected from $CH_2$, O, S and NH and n is an integer from 3-5, and

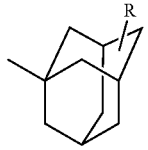

where R is $(CH_2)_nCH_3$ and n is a maximum of 7.

10. The method of claim 8 wherein $R_1$ and $R_3$ are each OH and $R_2$ is selected from $(CH_2)_nC\equiv CH$ where n is an integer from 3-5, $C\equiv C(CH_2)_nCH_3$ where n is an integer from 2-4,

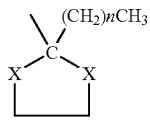

where each X is independently selected from $CH_2$, O, S and NH and n is an integer from 3-5, and

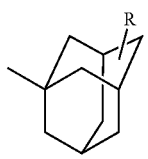

where R is $(CH_2)_nCH_3$ and n is a maximum of 7.

11. The method of claim 8 wherein:
$R_1$ is selected from OH; $NH_2$; $O(CH_2)_nN(CH_3)_2$ and

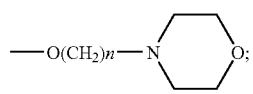

where n is an integer from 1-3;
$R_2$ is selected from $C(CH_3)_2(CH_2)_nCH_3$, where n is an integer from 3-5;

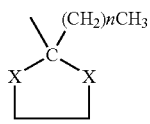

where each X is independently selected from $CH_2$, O, S and NH and n is an integer from 3-5; and

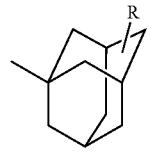

where R is $(CH_2)_nCH_3$, and n is a maximum of 7; and
$R_3$ is selected from H; OH; $OCH_3$; $N_3$ and $O(CH_2)_nOH$; where n is an integer from 1-5.

12. The method of claim 1 wherein $R_1$ and $R_3$ are each OH and $R_2$ is

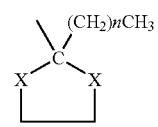

where each X is $CH_2$.

13. The method of claim 5 wherein $R_1$ and $R_3$ are each OH and $R_2$ is

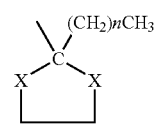

where each X is $CH_2$.

14. The method of claim 5 wherein $R_1$ and $R_3$ are each OH and $R_2$ is 1,1-dimethylheptyl.

15. The method of claim 8 wherein $R_1$ and $R_3$ are each OH and $R_2$ is

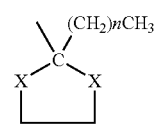

where each X is $CH_2$.

16. The method of claim 8 wherein $R_1$ and $R_3$ are each OH and $R_2$ is 1,1-dimethyl-6-heptynyl.

17. The method of claim 1 wherein the compound is substantially purified.

18. The method of claim 5 wherein the compound is substantially purified.

19. The method of claim 8 wherein the compound is substantially purified.

20. The method of claim 8 wherein the condition is selected from pain, peripheral pain, glaucoma, nausea and decreased appetite.

* * * * *